United States Patent [19]

Henderson

[11] Patent Number: 4,595,172
[45] Date of Patent: Jun. 17, 1986

[54] VENT VALVES FOR PROSTHETIC DEVICES

[76] Inventor: Gene Henderson, 11285 Clinton Bar Rd., Pine Grove, Calif. 95665

[21] Appl. No.: 717,948

[22] Filed: Mar. 29, 1985

[51] Int. Cl.$^4$ .............................................. F16K 1/38
[52] U.S. Cl. .................................. 251/321; 251/339; 137/903; 220/367
[58] Field of Search ................ 137/DIG. 4; 251/320, 251/321, 339; 220/367

[56] References Cited

U.S. PATENT DOCUMENTS

| 2,160,398 | 5/1939 | Crowley | 251/321 X |
| 3,433,456 | 3/1969 | Mueller | 251/339 |
| 4,457,487 | 7/1984 | Steigerwald | 137/DIG. 4 |

FOREIGN PATENT DOCUMENTS 2138109A 10/1984 United Kingdom ................ 251/339

Primary Examiner—Arnold Rosenthal
Attorney, Agent, or Firm—Manfred M. Warren; Robert C. Chickering; Glen R. Grunewald

[57] ABSTRACT

A valve especially designed for use in a prosthetic device such as an artificial limb wherein the limb stump is mounted within a mating socket provided by the prosthetic device and is firmly secured therein by vacuum sealing, the valve being is connected to vent the lower portion of the prosthesis socket when manually actuated. The valve includes a central core section of elastomeric material which is formed with a passageway therethrough for venting the prosthesis cavity and which is formed with an enlarged valve chamber and a valve set facing away from the prosthesis cavity. A valve member is mounted in the chamber and is moveable to and from the set to provide sealed and vented positions respectively. The movement of the valve is controlled by a finger engaging button which is in turn biased by elastomeric nodules to move the valve member to its seat thereby sealing the prosthesis chamber. The valve member may be moved to an open, venting position by depression of the operating button against the resilient resistance of the elastomeric nodules.

5 Claims, 6 Drawing Figures

VENT VALVES FOR PROSTHETIC DEVICES

BACKGROUND OF THE INVENTION

The invention relates to valves commonly used in prosthetic devices such as artificial limbs and the like wherein the limb stump is mounted within a mating socket provided by the prosthetic device and is firmly secured therein by vacuum sealing.

Prostheses designed for attachment to limb stumps are customarily formed with a recess which snuggly receives and fits the stump when inserted, with the recess being somewhat deeper than the stump so that a small chamber is left between the end of the stump and the bottom of the recess. A valve is mounted in the wall of the prosthesis in a passage venting the chamber upon insertion of the stump and which is closed upon such insertion so that thereafter the prosthesis is secured by the sealed bottom chamber to the stump. The valve may be operated when it is desired to make adjustments in the position of the prosthesis as required for comfortable wear during the day and for removal of the prosthesis from the stump.

Valves commonly used in prostheses with which applicant is familiar are mounted within an internally threaded ring, which in turn, is bonded in sealed relation within the wall of the prosthetic device adjacent the chamber. To operate the valve the wearer pulls outward on a valve stem, which is spring loaded and automatically returns to the closed position when released.

Valves heretofore available have been awkward to use and are composed of a number of parts inviting a failure of operation of one or more of the parts and hence prevent the use of the prosthesis pending repair or replacement of the valve. Additionally, with the valve stem extending outwardly from the surface of the prosthesis, an unsightly bulge may be apparent in the wearer's clothing, and when opening the valve, the wearer must grasp the valve stem through clothing which if the clothing is heavy makes this operation difficult. If the clothing is tight fitting the outwardly protruding stem may readily wear the adjacent clothing.

SUMMARY OF THE INVENTION

An object of the present invention is to provide a valve of the character described which is substantially flush with the surface of the prosthesis such that it does not cause a bulge in the wearer's clothing or cause premature wear in the clothing.

Another object of the present invention is to provide a valve of the character described above that can be easily operated with one finger, leaving the wearer's hands free to adjust the position of the prosthesis.

A further object is to provide a vent valve having a minimum number of sturdily formed parts designed for long and dependable life and easy and inexpensive replacement when required.

Still another object of the invention is to provide a valve which is compatible with older style valves already in use in that the valve of the present invention can be threaded into the standard internally threaded ring member customarily mounted in the wall of the prosthetic device.

The invention possesses other objects and features of advantage, some of which of the foregoing will be set forth in the following description of the preferred form of the invention which is illustrated in the drawings accompanying and forming part of this specification. It is to be understood, however, that variations in the showing made by the said drawings and description may be adopted within the scope of the invention as set forth in the claims.

DETAILED DESCRIPTION OF THE INVENTION

Figure 1:
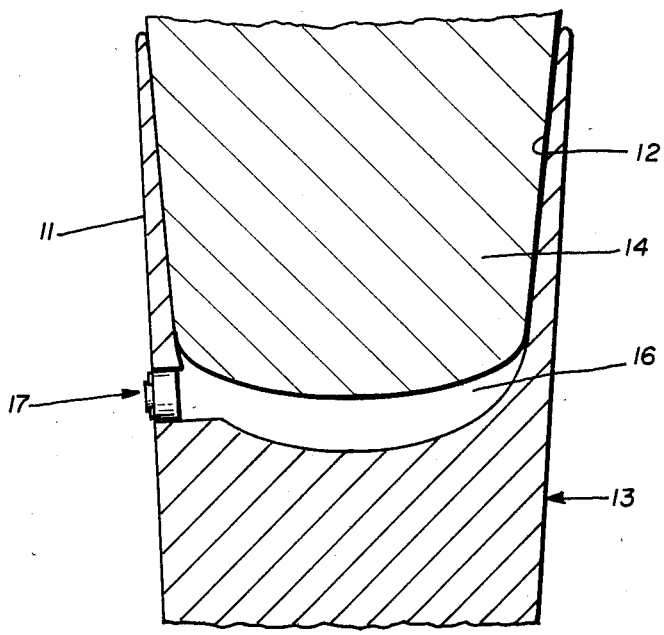
FIG. 1 is a cross-sectional view of the interfitting stump and prosthetic device and the valve of the present invention.

The valve of the present invention is designed for mounting in a wall 11 of a recess 12 formed in a prosthetic device 13 which is formed and dimensioned to receive, in a mating snug fit the end of a limb stump 14 with which the prosthetic device is to be used. As will be observed there is a mated, sealed fit between stump 14 and recess 12, and the parts are formed and dimensioned with the recess slightly deeper than the length of the stump inserted therein so as to leave a small chamber 16 to which the valve 17 of the present invention is connected.

The present valve comprises briefly, an elastomeric body 18 which is mounted in sealed relation in wall 11 and is formed with a passageway 19 therethrough venting chamber 16 to the atmosphere, the passageway 19 being formed with an enlarged cavity 21 providing a valve seat 22 facing away from chamber 16; a valve member 23 mounted in cavity 21 and moveable to and from seat 22 to provide sealed and vented positions respectively for the chamber and passageway 19; means 26 integral with elastomeric body 18 biasing valve member 23 to its sealed position; and a stem 27 on valve member 23 which extends through and to the exterior of passageway 19 and is disposed for manual engagement and displacement against the resistance of biasing means 26 to displace valve member 23 to its vented position. To facilitate this latter operation a manually engageable button 31 is mounted on the outer end of stem 27 in postion for engagement by a single finger for depression against the biasing means 26 for displacing valve member 23 away from seat 22 thereby opening passageway 19 for venting of chamber 16.

Figure 2:
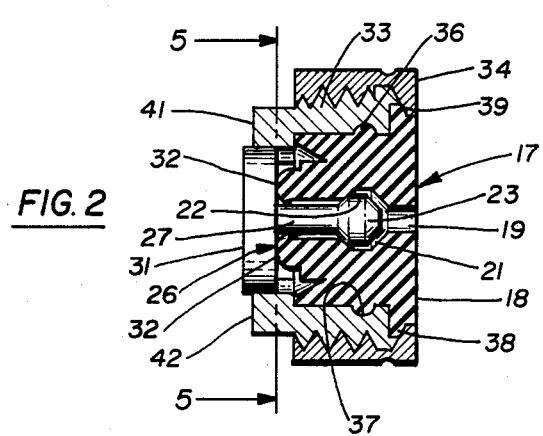
FIG. 2 is an enlarged cross-sectional view of the valve of the present invention in its normally closed, sealed position.
Figure 3:
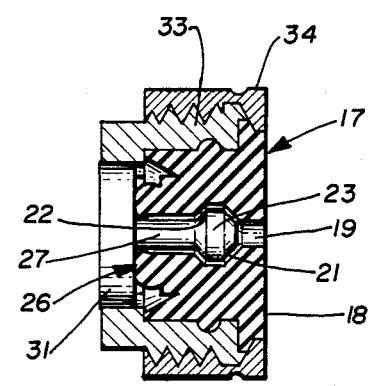
FIG. 3 is a cross-sectional view similar to FIG. 2 but showing the valve in open or venting position.
Figures 4, 5, 6:
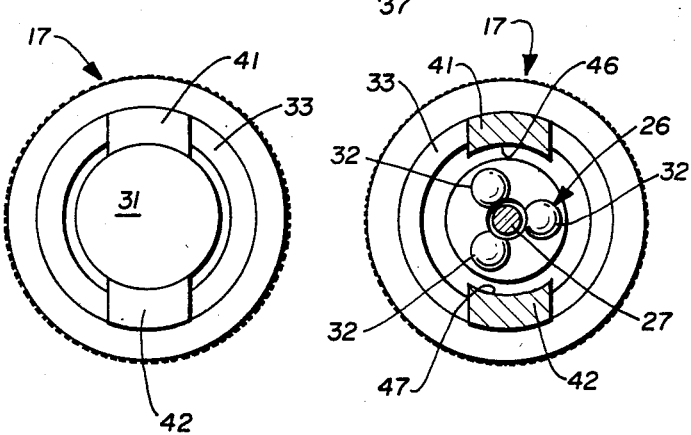
FIG. 4 is a front elevation of the valve.
FIG. 5 is a cross-sectional view taken substantially on the plane of line 5—5 of FIG. 2.
FIG. 6 is a rear elevation of the valve.

As a feature of the illustrated embodiment biasing means 26 here includes a plurality of elastomeric nodules 32 formed integrally with elastomeric body 18. As will be best seen in FIG. 5, these nodules are formed in substantially equally circumferentially spaced relation around passageway 19 and are at least three in number so as to provide a balanced engagement with the underside of button 31 and a balanced support therefore, normally positioning valve member 23 in its sealed position when the nodules are uncompressed. The nodules being formed of elastomeric material are designed for compression upon inwardly displacement of button 31 so as to move valve member 23 to its open or vented position against the resilient resistance of the compressed nodules. This action can best be seen by comparing the position of the parts in FIGS. 2 and 3.

As another feature of the present invention elastomeric body 18 is mounted in an externally threaded ring member 33 which surrounds the elastomeric body and is formed for threading into an internally threaded ring member 34 which may or may not be provided by the manufacturer of the prosthetic device and threaded in wall 11. If not so supplied ring member 34 will be suitably bonded into a circular opening formed in wall 11 in registration with chamber 16. The elastomeric body is preferably formed with a rib which is mounted in a locating recess 37 formed in the internal wall of member 33, and is formed with an inner end flange 38 which is compressed between the inner end of ring member 33 and an internal flange 39 formed on ring member 34.

As a further feature of the illustrated embodiment, ring member 33 is formed with upstanding guard portions 41 and 42 which are formed with arcuate surfaces 46 and 47 on diametrically opposite sides of button 31 and between which button 31 is nested for guided reciprocation in operating valve member 23. As will be observed the size of nodules 32 and other parts is such that the engageable outside face of button 32 is only slightly extended from guard portions 41 and 42 so as to minimize the external protrusion of a valve operating member. When the valve member is moved to the open position the outside of the operating button will be substantially flush with the adjacent exterior faces of guard portions 41 and 42, see FIG. 3. This displacement of the valve member may be effected merely by pressure of one finger of the user while leaving the user's hands free to adjust the position of the prosthetic device. As will be further observed the construction of the present valve is neat causing a minimum bulge in the wearer's clothing or a premature wear of the clothing; and is accomplished by the use of a miniumum number of sturdily formed parts designed for long and dependable life and easy and inexpensive replacement when required.

What is claimed is:

1. A vent valve for mounting in a wall of a low pressure chamber comprising, an elastomeric body mounted in sealed relation in said wall and having a passageway therethrough venting said chamber to the atmosphere, said passageway being formed with an enlarged cavity providing a valve seat facing away from said chamber;

a valve member mounted in said cavity and having a stem extending to the exterior of said body and a button on the outer end of said stem adapted for manual engagement for moving said valve member from said seat to provide a vented position for said chamber; and biasing means including a plurality of elastomeric nodules on said elastomeric body surrounding said passageway and positioned for engagement with said button for normally positioning said valve member in sealed position in said seat, said nodules being formed for compression upon inward displacement of said button to move said valve to said vented position.

2. The vent valve as defined in claim 1, an externally threaded ring member surrounding said elastomeric body and formed for threading into an internally threaded ring member and for sealing said elastomeric body therebetween.

3. The vent valve as defined in claim 2, said body being formed with an integral, annular body flange, said internally threaded ring member being formed with an internal flange providing a seat for one side of said elastomeric body flange, and said externally threaded ring member being formed for engagement with the opposite side of said body flange for sealing of said elastomeric body in said wall.

4. The vent valve as defined in claim 3, said body having an annular rib, an internal surface of said externally threaded ring member having an annular recess dimensioned to receive said rib, for locating said elastomeric body therein.

5. The vent valve as defined in claim 4, said externally threaded ring member being formed with upstanding guard portions, said button being nested within said portions for guiding said button for reciprocation of said valve member.

* * * * *